United States Patent [19]

Horacek et al.

[11] Patent Number: 5,130,444
[45] Date of Patent: Jul. 14, 1992

[54] BISMALEIMIDES AND THEIR USE IN PREPARING POLYIMIDES

[75] Inventors: Heinz Horacek, Linz; Gerd Greber, Bad Vöslau, both of Austria

[73] Assignee: PCD Polymere Gesellschaft m.b.H., Schwechat-Mannsworth, Austria

[21] Appl. No.: 466,385

[22] PCT Filed: Nov. 10, 1988

[86] PCT No.: PCT/EP88/01018
    § 371 Date: Apr. 24, 1990
    § 102(e) Date: Apr. 24, 1990

[87] PCT Pub. No.: WO89/04850
    PCT Pub. Date: Jun. 1, 1989

[30] Foreign Application Priority Data

Nov. 18, 1987 [AT] Austria .................. 3039/87

[51] Int. Cl.$^5$ ............... C07D 207/452; C08G 73/12
[52] U.S. Cl. ................. 548/521; 528/353; 528/337; 528/336
[58] Field of Search .......... 548/521; 518/353

[56] References Cited

U.S. PATENT DOCUMENTS 4,128,598 12/1978 Makino et al. ............. 260/837 R
4,759,987 7/1988 Mizobe et al. ............. 428/395

OTHER PUBLICATIONS

Kwiatkowski et al., Journal of Polymer Science, Poly. Chem. Ed., 13, 961-972 (1975).
A. Harvey, Hochmolekularbericht 1987, H.4082/87, Reg. of Annu. Tech. Conf. Soc. Plast. Eng. 32, 1311-1315 (1986)—Abstract.

*Primary Examiner*—David B. Springer
*Attorney, Agent, or Firm*—Wenderoth, Lind & Ponack

[57] ABSTRACT

Bismaleimides of the formula I

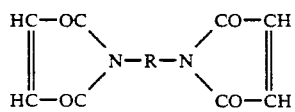

wherein R denotes a radical of the formula II

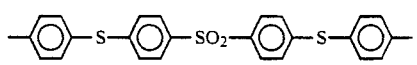

and polyimides which can be prepared from these bismaleimides, if appropriate with the addition of an aromatic diamine. The polyimides are optionally reinforced with fibers.

2 Claims, No Drawings

BISMALEIMIDES AND THEIR USE IN PREPARING POLYIMIDES

DESCRIPTION

The invention relates to bismaleimides and optionally fiber-reinforced polyimides prepared therefrom.

Polyimides based on bismaleimides are already known from U.S. Pat. No. 3,380,964, and they can be prepared by heating the bismaleimides at temperatures of 80° to 400° C., ethylene-bis-maleimide, diphenylmethane-bis-maleimide, diphenyl ether-bis-maleimide or diphenyl sulfone-bis-maleimide, inter alia, being used.

The known polyimides are distinguished by a heat stability which is very high for plastics. However, they have the disadvantage that they are very brittle and can be further processed only to a limited degree. For example, only hard and brittle laminates can be produced from them.

The object of the invention was therefore to discover dismaleimides which can be polymerized to flexible and less brittle polyimides which are optionally reinforced with fibers and if appropriate can be brought into the final shape by subsequent compression molding.

The object of the invention has been achieved with the aid of novel bismaleimides which contain aromatics as chain elements bonded via —S— and —SOhd 2— bridges and from which polyimides with improved properties can be prepared.

The invention accordingly relates to bismaleimides of the formula I as follows

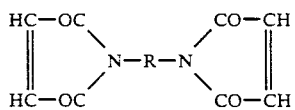

in which R denotes a radical of the formula II as follows

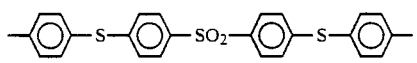

The bismaleimides according to the invention are prepared by reacting the diamine of the formula III as follows

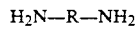

with maleic acid or a maleic acid derivative. Preferably, the diamine of the formula III

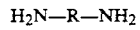

is reacted with maleic anhydride. The reaction takes place particularly well in polar solvents, such as, for example, dimethylformamide, dimethylacetamide, dimethyl sulfoxide, N-methylpyrrolidone (NMP), tetramethylurea or hexamethylphosphoric acid triamide.

The diamine of the formula III, 1,4-bis-(4-aminophenylthio)diphenyl sulfone (BDS) is obtained, for example, in accordance with ER-A-0,245,815 by reaction of the Na salt of bis-(4-mercaptophenyl)diphenyl sulfone with excess 4-chloronitrobenzene to give 1,4-bis-(4-nitrophenylthio)diphenyl sulfone and subsequent reduction of the nitro groups.

The bismaleimides according to the invention can be used for the preparation of polyimides with improved properties. The bismaleimides can be polymerized either by themselves or together with an aromatic diamine to give polyimides. Possible aromatic diamines are all the diamines known in polyamide and polyimide chemistry. Suitable diamines are, for example, those based on aromatic, fused aromatic or heteroaromatic rings, which are optionally further substituted, for example by alkyl or alkoxy groups or by halogen atoms. The diamine can be built up from either one or more rings, the rings being bonded to one another directly or via bridge members. Examples of suitable bridge members are —O—, —CH$_2$—, —C(CH$_3$)$_2$, —C(CF$_3$)$_2$—, —S—, —SO—, —SO$_2$—, —CO—, —CO—O—, —CO—NH—, —N=—, —NH—, —N(alkyl)— having 1 to 6 C atoms in the alkyl radical and —N(aryl)— having 6 to 20 C atoms in the aryl radical.

Examples of possible aromatic diamines are: 1,4-phenylenediamine, 4,4'-diaminodiphenyl, 4,4'-diaminodiphenylmethane, 4,4'-diaminodiphenyl sulfone, 4,4'-diaminodiphenyl ether, 4,4'-diaminobenzophenone, 4,4'-methylenebis(o-chloroaniline), 1,2-bis(2-aminophenylthio) propane, diisopropyl methylenedianthranilate, 4,4'-methylene-bis-2,6-diisopropylaniline, propyl 3,5-diamino-4-chlorobenzoate, 4,4'-diamino-5,5'-dimethylphenyl-2,2'-disulfonic acid, 5(6)-amino-11-(4-aminophenyl)-1,3,3-trimethylindane, 5,5'-diamino-2,2'-bipyridyl sulfide, 2,4-diethyltoluidinediamine, 4,4'-diaminobisbenzophenone, dioxyphenylenebisaminopyridine and 2,5-diamino-1,3,4-thiadiazole.

The diamine of the formula III

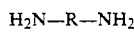

1,4-bis(4-aminophenylthio)diphenyl sulfone, is preferred.

The invention furthermore relates to the polyimides prepared from the bismaleimides according to the invention. The polyimides consist of recurring monomeric units of bismaleimides of the formula IV

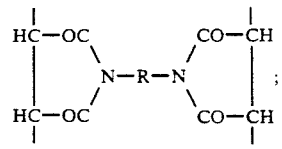

the polymer bond being via the double bonds of the maleimide radicals where bismaleimides are used, and addition of the NH$_2$ groups of the diamine onto the double bond of the maleimide radical also taking place where bismaleimide and diamine are used. Polyimides which are built up from 0 to 1 mole of diamine per mole of bismaleimide are preferred, a molar ratio of diamine to bismaleimide of 0.1:1 to 0.6:1 being particularly preferred. The viscosity of the polyimides according to the invention is in the range from 100 to 1,000 mPas, measured in 50% strength by weight freshly prepared solutions in NMP at 23° C. (Brookfield viscometer, spindle 3).

The polyimides according to the invention have a good temperature stability up to about 400° C. and very good mechanical and electrical properties, thus, above all, a very good impact strength. The mechanical properties show no noticeable decline up to temperatures of about 250° C.

On the basis of their solubility, especially in the abovementioned polar solvents, and on the basis of their fusibility in the not completely hardened state, they can be further processed very easily, for example to fibers, films, sheets or moldings. At the same time, the polyimides can advantageously be reinforced with fibers for certain used for further improvement of the mechanical properties, it being possible to use short fibers, fiber mats, woven fabric or unidirectional fiber rovings or laid fiber fabrics for reinforcement. The content of reinforcing fibers in the composite is usually about 20–70% by weight. The fiber mats can consist either of cut fibers or of continuous filaments deposited as a non-woven material, it being possible for the fibers and filaments to be either in a tangled position or aligned. The fiber mats are preferably compacted mechanically, for example by needling, stitching or quilting. The weight per unit area of the fiber mats is usually 250–1,200 g/m², and that of woven fabrics is preferably 50–300 g/m².

Glass fibers, carbon fibers or aramid fibers or mixtures of these fibers, for example, can be used according to the requirements of the mechanical properties. Carbon fibers or aramid fibers are used above all where special requirements are particularly imposed on the strength, rigidity and low specific gravity of the components produced from the polyimides.

In many cases, it proves to be particularly advantageous not to harden the polyimides completely, so that they can still be further processed, that is to say still remain deformable, fusible and thermocurable, and if appropriate can still be reshaped into a finished component in a subsequent hot press molding operation. This is of importance in the case of prepregs which consist of, for example, only partly hardened polyimides reinforced with woven fiber fabrics or rovings, are stable on storage and can also still be hot press molded to the desired finished component months later.

The polyimides according to the invention are prepared by heating the bismaleimide of the formula I

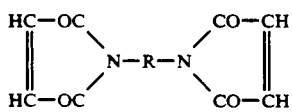

if appropriate together with an aromatic diamine, at temperatures of about 100° to 300° C. More or less complete hardening of the polyimide resin takes place according to the temperature chosen and the duration of the heating. Heating is preferably carried out in two stages, the mixture being heated to temperatures of about 100° to 180° C. in the first stage, depending on the duration of the heating, and a polyimide which is not completely hardened being in this way obtained. For example, the bismaleimide and diamine can be heated at 140° C. for 10 minutes or at 150° C. for 5 minutes or at 165° C. for 2 minutes, in which case the starting materials sinter and partly polymerize. The starting materials are advantageously ground before and after the sintering. If appropriate, the incompletely polymerized polyimide is brought together with fiber reinforcement, and can then be hardened completely in a second state by further heating at temperatures of 120° to 300° C. under a pressure of 1 to 20 bar.

Complete hardening can be achieved, for example, during heat treatment at 200° C. for 60 minutes, or at 250° C. for 30 minutes under a pressure of 15 bar. To achieve the optimum mechanical properties, subsequent conditioning for several hours is necessary. For example, conditioning can be carried out at 200° C. for 48 hours or at 25° C. for 24 hours, under normal pressure.

To prepare fiber-reinforced polyimide resins, for example, the reinforcing fibers can be brought together with the bismaleimide and if appropriate the diamine and the mixture can then be heated to form the polyimide resin. It is also possible for the fibers to be brought together with the already partly hardened polyimide powder. Fiber-reinforced laminates or prepregs are produced, for example, by applying the finely ground powder, for example from a hopper, onto a fiber reinforcement web, or by impregnating the reinforcement web with a solution and subsequently heating the webs, if appropriate under pressure. The fiber-reinforced laminates and prepregs are particularly advantageously produced continuously. In this production, the pulverulent, partly hardened polyimide is metered, for example, onto the belt of a twin-belt press and at the same time one or more layers of the fiber reinforcement, in the form of a woven fabric, a roving, a lining or a mat, is also allowed to run into the press. In the twin-belt press, the woven fabrics, rovings, laid fabrics or mats are impregnated with the molten polyimide at temperatures of 100° to 300° C. under pressures of 1 to 20 bar, complete hardening also being possible, depending on the residence time and temperature. In the case of solvent impregnation, the reinforcement web is passed, for example, through a trough containing an approximately 40–60% strength by weight solution of the partly hardened polyimide in a polar solvent, for example in N-methylpyrrolidone. The amount applied is adjusted via a doctor blade and squeeze rolls. The impregnated webs are dried, for example, in a vertical or horizontal drying tunnel. The only partly hardened fiber-reinforced polyimides (prepregs) can be processed or reshaped to a completely hardened finished component, for example to printed circuit boards, electrical coil cores, components of combustion engines or equipment components for air and space travel, under the action of pressure and temperature in a later processing step.

EXAMPLE 1 a) Preparation of the bismaleimide 23.5 g (0.05 mol) of 1,4-bis(4-aminophenylthio)diphenyl sulfone (BDS) were dissolved in 80 g of dimethylformamide (DMF) in a 250 ml flask, while flushing with nitrogen, and the solution was cooled to −20° C. 9.8 g (0.1 mol) of maleic anhydride (MA), dissolved in 20 g of DMF, were then slowly added dropwise, while stirring, so that the temperature of the reaction mixture did not exceed −15° C. The mixture was then stirred at −15° C. for a further 45 minutes, after which 1.0 g of anhydrous Na acetate and 15 g of acetic anhydride were added to the orange-colored solution, which slowly turned brown, at −15° C. and the solution was heated to 55° C. and further stirred at this temperature for 1 hour. After cooling, the solution was added dropwise to a mixture of ice and water, after which a brown precipitate separated out and was filtered off with suction, washed with water and dried at 80° C. in vacuo.

28.4 g (90% of theory) of 1,4-bis(4-maleimidophenyl-thio)diphenyl sulfone having a melting point of 140° C. were obtained.

b) preparation of the polyimide 1 mol of the bismaleimide obtained according to Example 1a was ground with 0.4 mol of BDS and the mixture was then sintered at 150° C. for 10 minutes. The fusible polyimide obtained in this way was ground to a powder. The melting point was 135°–185° C. The viscosity of a 50% strength freshly prepared solution in NMP at 23° C. was 300 mPas (Brookfield viscometer).

c) production of a Laminate

40% by weight, based on the finished composite, of the polyimide powder obtained in Example 1b was applied to a 20×20 cm glass woven fabric (No. 92626, Interglas) with a weight per unit area of 296 g/m². The system was then heated at 200° C. for 3 minutes under atmospheric pressure, pressed at 200° C. for 1 hour under a pressure of 15 bar and finally conditioned at 200° C. for 48 hours.

A flexible laminate was obtained; the properties are summarized in Table 1.

EXAMPLE 2 a) Preparation of the polyimide

The bismaleimide obtained according to Example 1a was sintered at 200° C. for 10 minutes. The fusible polyimide obtained in this way was ground to a powder. The melting point of the yellow powder as 125°–190° C.

b) Production of a Laminate

The polyimide powder obtained according to Example 2a was applied in an amount of 40% by weight to a glass woven fabric analogously to Example 1c and the system was pressed at 200°0 C. under 15 bar for 1 hour and conditioned for 48 hours. The properties of the resulting laminate are summarized in Table 1.

EXAMPLE 3 a) Preparation of the polyimide 1 mol of the bismaleimide obtained according to Example 1a was ground with 1 mol of BDS and the mixture was then sintered at 150° C. for 10 minutes. The fusible polyimide obtained in this way was ground to a powder. The melting point was 160°–220° C.

b) Production of a prepreg

40% by weight of the polyimide powder obtained according to Example 3a was pressed with 60% by weight of a glass woven fabric (No. 92626, Interglas) at 150° C. under a pressure of 15 bar for 1 minute to give a prepreg which can be further processed as a thermoplastic.

c) Production of a laminate

The prepreg obtained according to Example 3b was pressed at 200° C. under 15 bar for 1 hour and then conditioned at 200° C. under atmospheric pressure for 48 hours. The properties of the resulting laminate are summarized in Table 1.

EXAMPLE 4 a) Preparation of the polyimide 1 mol of the bismaleimide obtained according to Example 1a was ground with 0.4 mol of 4,4'-diaminodiphenyl ether and the mixture was then sintered at 150° C. for 5 minutes. The fusible polyimide obtained in this way was then ground to a powder. The softening range was 160°–300° C.

b) Production of a laminate

40% by weight, based on the finished composite, of the polyimide powder obtained in Example 4a was applied as a 50% strength solution in NMP to a 20×20 cm glass woven fabric (No. 92626, Interglas). The system was then heated at 200° C. under atmospheric pressure for 3 minutes, pressed at 200° C. under a pressure of 15 bar for 1 hour and finally conditioned at 200° C. for 48 hours. A laminate with the physical values of Table 1 is obtained.

A laminate with the same properties was obtained when the polyimide obtained according to Example 4a was applied as a powder to the glass fiber woven fabric.

TABLE 1

|  |  | Example |  |  |  |
|---|---|---|---|---|---|
|  |  | 1 | 2 | 3 | 4 |
| Bismaleimide:diamine | (mol:mol) | 1:0.4 | 1:0 | 1:1 | 1:0.4 |
| Diamine |  | BDS[1] | BDS[1] | BDS[1] | DAE[2] |
| Tensile strength DIN 53455 | N/mm² | 520 | 450 | 215 | 290 |
| Elongation DIN 53455 | % | 5.2 | 2.1 | 7.0 | 1.5 |
| Flexural E modulus DIN 53457 | N/mm² | 28000 | 32000 | 15000 | 23000 |
| Resin content | % | 40 | 40 | 40 | 40 |
| Bulk density | g/cm³ | 1.69 | 1.72 | 1.70 | 1.71 |
| Impact strength Din 53453 according to Izod | J/m | 950 | 1000 | 1200 | 1100 |
| Compressive strength DIN 53454 | N/mm² | 340 | 400 | 250 | 380 |
| Delamination resistance | N/mm² | 16 | 14 | 17 | 18 |
| ASTM-D-2345 Specific volume resistivity | Ohm · cm | $6.10^{14}$ | $5.5.10^{14}$ | $5.10^{14}$ | $6.10^{14}$ |
| ASTM-D-257 1kHZ Dielectric constants |  | 4.6 | 4.7 | 4.8 | 4.6 |
| ASTM-D-150 1kHZ Dielectric loss |  | $1.1.10^{-2}$ | $1.0.10^{-2}$ | $1.3.10^{-2}$ | $1.2.10^{-2}$ |

TABLE 1-continued

| | Example | | | |
|---|---|---|---|---|
| | 1 | 2 | 3 | 4 | factor
tan delta at 1kHZ

[1] 1,4-bis(aminophenylthio)diphenyl sulfone
[2] 4,4'-diaminodiphenyl ether

We claim:

1. A bismaleimide of the formula I

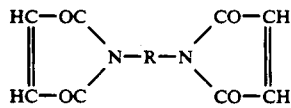

wherein R denotes a radical of the formula

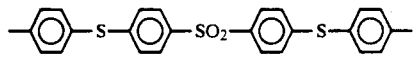

2. The use of a bismaleimide as claimed in claim 1 for the preparation of polyimides consisting of recurring monomeric units of a bismaleimide of the formula IV

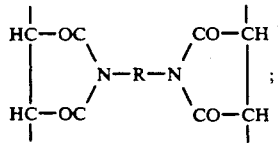

0 to 1 mol of an aromatic diamine per mol of bismaleimide additionally being added onto the maleimide groups.

* * * * *